United States Patent [19]
Ishizaka et al.

[11] Patent Number: 5,096,828
[45] Date of Patent: Mar. 17, 1992

[54] BIOCHEMICAL ANALYSIS METHOD

[75] Inventors: Hideo Ishizaka; Yukihide Miyata, both of Kanagawa, Japan

[73] Assignee: Fuji Photo Film Co., Ltd., Kanagawa, Japan

[21] Appl. No.: 680,792

[22] Filed: Apr. 3, 1991

Related U.S. Application Data

[63] Continuation of Ser. No. 282,230, Dec. 9, 1988, abandoned.

[30] Foreign Application Priority Data

Dec. 25, 1987 [JP] Japan .................. 62-328699
Dec. 25, 1987 [JP] Japan .................. 62-328700

[51] Int. Cl.$^5$ .................................. G01N 35/00
[52] U.S. Cl. ............................. 436/44; 422/66; 422/67; 436/165; 356/440
[58] Field of Search .............. 436/44, 165; 422/66, 422/65, 67, 104; 356/440, 443, 243, 244

[56] References Cited

U.S. PATENT DOCUMENTS

| | | | |
|---|---|---|---|
| 3,526,480 | 9/1970 | Findl et al. | 422/66 |
| 3,904,369 | 9/1975 | Alder et al. | 422/66 |
| 3,992,158 | 11/1976 | Przybylowicz et al. | |
| 4,863,693 | 9/1989 | Howell | 422/66 |

FOREIGN PATENT DOCUMENTS 53-21677 7/1978 Japan .
55-164356 12/1980 Japan .
56-77746 6/1981 Japan .

*Primary Examiner*—Robert J. Warden
*Assistant Examiner*—Lyle A. Alexander
*Attorney, Agent, or Firm*—Sughrue, Mion, Zinn, Macpeak & Seas

[57] ABSTRACT

A biochemical analysis method comprises the steps of accommodating a long test film in a refrigerator, repeatedly pulling the long test film out of the refrigerator until a sample-applying portion, i.e., the next unused portion of the test film, is aligned with a sample applying position, applying a liquid samples onto the sample-applying portions of the long test film at which time the sample-applying portions become sample-applied portions, incubating the sample-applied portions, and irradiating light to the sample-applied portions in order to determine optical densities, which depend on the how much of a certain constituent in a liquid sample existed and therefore reacted with a reagent in a reagent layer of the test film. The length of a sample-applying portion to which a present sample will be applied, is changed in accordance with conditions which exist after the analysis of the sample applied to the test film immediately prior to the present sample has been finished. Alternatively, nearly the whole sample-applying portion that was positioned upstream from the sample-applied portion is pulled back into the refrigerator after the above mentioned measurement of the optical density is completed, and is pulled out prior to the next application of a sample so that the sample-applying portion positioned in the refrigerator is brought to the sample applying position.

9 Claims, 6 Drawing Sheets

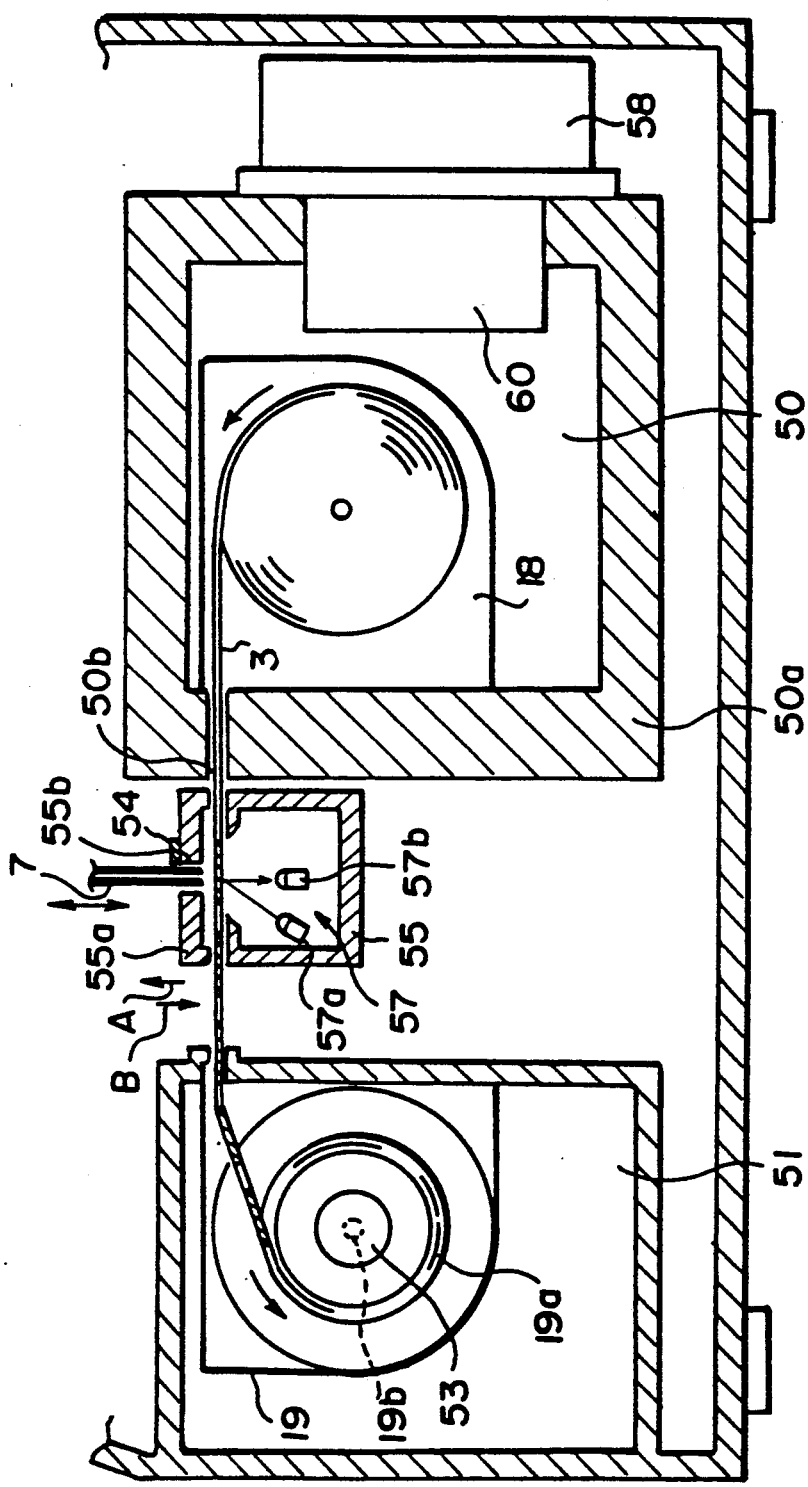

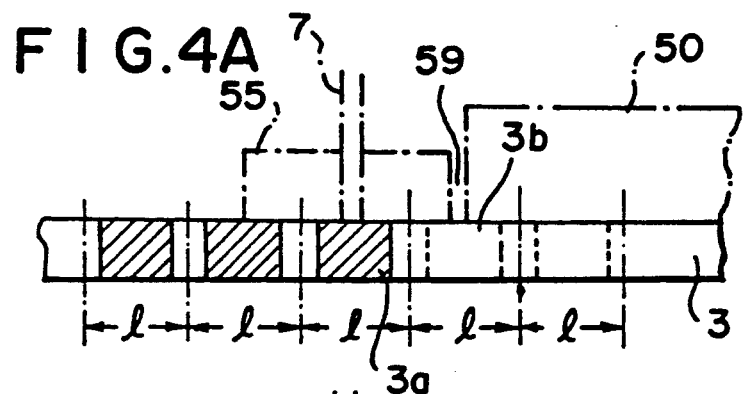
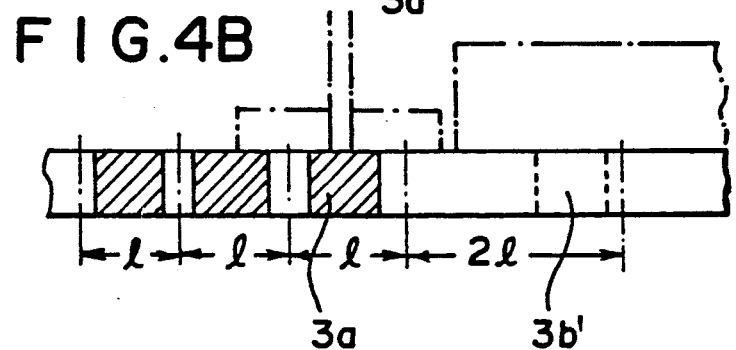
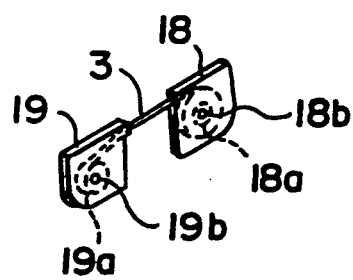

BIOCHEMICAL ANALYSIS METHOD

This is a continuation of application Ser. No. 07/282,230 filed Dec. 9, 1988, now abandoned.

BACKGROUND OF THE INVENTION

1. Field of the Invention

This invention relates to a biochemical analysis method for applying a liquid sample to a long test film provided with a single reagent layer or a plurality of reagent layers, maintaining the long test film at a predetermined temperature (i.e. carrying out incubation) for a predetermined time, and measuring the optical density of the product formed by a reaction of a reagent in the reagent layer with the liquid sample during or after the incubation. This invention particularly relates to a biochemical analysis method enabling accurate measurement of the quantities of a products formed by reactions taking place on a long test film.

2. Description of the Prior Art

Qualitative or quantitative analysis of a specific chemical constituent in a liquid sample is generally conducted for various industrial purposes. Particularly, it is very important in biochemical and clinical fields to quantitatively analyze chemical constituents or physical constituents in body fluid such as blood or urine.

Recently, as disclosed in, for example, Japanese Patent Publication No. 53(1978)-21677 and Japanese Unexamined Patent Publication No. 55(1980)-164356, a dry type chemical analysis slide was developed for use in a system for quantitatively analyzing a specific chemical constituent or a specific physical constituent contained in a liquid sample simply by applying a droplet of the liquid sample to the slide. With a method using the chemical analysis slide, it is possible to analyze a liquid sample more simply and more quickly than with a conventional wet type analysis method. Therefore, the use of the chemical analysis slide is desirable particularly in medical organizations, research laboratories, or the like where many samples are to be analyzed.

In order to analyze a chemical constituent or the like contained in a liquid sample by use of the chemical analysis slide, a measured amount of the liquid sample is put on the chemical analysis slide and is maintained at a predetermined temperature (i.e. incubated) for a predetermined time in an incubator to cause a color reaction. The chemical analysis slide is then exposed to light having a wavelength selected in advance, the selection of which wavelength depends on the constituents of the liquid sample and the constituents of a reagent contained in the reagent layer in the chemical analysis slide. Quantitative analysis of the chemical constituents or the like in a sample is carried out by irradiating a reaction product formed on a chemical analysis slide and finding the ratio of transmitted vs. reflected light.

In medical organizations, research laboratories or the like where many liquid samples are analyzed, it is desirable to conduct the analysis automatically and sequentially. To satisfy this need, various chemical analysis apparatuses have been proposed, which by use the aforesaid chemical analysis slides. One of such chemical analysis apparatuses is disclosed in, for example, Japanese Unexamined Patent Publication No. 56(1981)-77746. Also, as a means for analyzing liquid samples automatically and sequentially, an apparatus is proposed in, for example, U.S. Pat. No. 3,526,480 wherein a long tape-like test film containing a reagent is used instead of the aforesaid chemical analysis slides, and sample application, incubation and measurement are carried out sequentially on adjacent portions of the test film. The running cost of the apparatus using the long tape-like test film is lower than the running cost of the apparatus using the chemical analysis slides, and measurements on many liquid samples can be carried out sequentially by use of a simple mechanism.

The long test film may be wound around a feed reel, for example and then loaded into the apparatus. The long test film is affected by temperature or humidity and will deteriorate (i.e., the chemical properties of the long test film will change) if the temperature and humidity are not closely controlled. Accordingly, the applicant proposed a biochemical analysis apparatus provided with a refrigerator kept at a low temperature and low humidity for accommodating the long test film so that it does not deteriorate if a long time occurs between when a long test film is loaded into the apparatus and when analysis begins. At the time at which analysis is to be carried out with the proposed biochemical analysis apparatus, the long test film is pulled out of the refrigerator by a test film conveyance means until an edge of a specific desired portion of the test film is aligned with a predetermined sample applying position, after which a liquid sample is applied onto the long test film, and incubation and measurement are then carried out. Therefore, when a plurality of liquid samples are to be analyzed sequentially by use of the long test film, the length of the portion of the long test film, which is pulled out sequentially by the test film conveyance means equals the minimum length necessary for a single analysis. The long test film is forwarded just before each liquid sample is applied onto the long test film.

However, the place at which the film exits from the refrigerator and the sample applying position are spaced somewhat apart from each other. Therefore, when a plurality of liquid samples are to be analyzed by moving the long test film forward in the manner mentioned above, part of the long test film to which the present sample is to be applied is pulled out of the refrigerator when the sample analyzed immediately prior to the present sample is applied. Therefore, a part of the long test film is not kept at as low a temperature and at as low a humidity as the film portions still in the refrigerator. Accordingly, if analysis is interrupted and a long time elapses prior to the application of a next liquid sample, the part of the long test film positioned outside of the refrigerator, and onto which a liquid sample has not yet been applied, deteriorates, and an accurate analysis of a sample applied to a deteriorated film portion cannot be done.

SUMMARY OF THE INVENTION

The primary object of the present invention is to provide a biochemical analysis method which enables accurate analysis of a sample applied to a portion of a long test film even though a time interval between consecutive applications of samples to adjacent portions of a long test film becomes long.

Another object of the present invention is to provide a biochemical analysis method which enables both accurate analysis of a sample applied to a portion of a long test film and efficient use of the test film even though a time interval between consecutive applications of samples to adjacent portions of the long test film becomes long.

The present invention provides a first biochemical analysis method comprising the steps of accommodating a long test film containing a reagent layer in a refrigerator, repeatedly pulling said long test film out of said refrigerator until a sample-applying portion, i.e. the next unused portion of the test film is aligned with predetermined sample applying position, sequentially applying liquid samples to the sample-applying portions of said long test film at which time the sample-applying portions become sample-applied portions, and a new sample-applying portion is defined as lying upstream from and adjacent to the sample-applied portion, for each analysis of a sample keeping said sample-applied portions of said long test film at a predetermined temperature for a predetermined time in an incubator, and thereafter irradiating light to said sample-applied portions of said long test film, and finding the optical densities which depend on how much of reaction product was formed by a reaction between a liquid sample and a reagent in the reagent layer of the long test film, wherein changing the length of the sample-applying portion, which is pulled out from said long test film accommodated in said refrigerator, prior to a next sample application to said long test film, in accordance with conditions after measurement has been finished (to be described below).

The term "conditions after measurement has been finished" as used herein means various conditions, which are present when the analysis of one sample is finished and an analysis of a next sample is to start and which are related to deterioration of the long test film. The term embraces the time elapsed between consecutive applications of samples, the temperature of the long test film, the humidity, the type of long test film used, and other conditions. The conditions may be any of or any combination of those listed above.

With the first biochemical analysis method in accordance with the present invention, when it is expected that part of a sample-applying portion of the long test film, which is to be used for the analysis of a present sample, has deteriorated because, for example, it was pulled out of the refrigerator at the start of the analysis of the last prior sample and a long time has elapsed since the last prior analysis, the length of the sample-applying portion of the long test film is increased so that the part of the sample-applying portion expected to be deteriorated is not used in the next analysis. Therefore, an accurate analysis of a sample can be carried out by using the part of the sample-applying portion which is known not to be deteriorated.

As mentioned above, with the first biochemical analysis method of the present invention, when a part of a sample-applying portion of the long test film remains outside the refrigerator for too long a period of time, the length of the sample-applying portion is increased and the amount of the long test film which is pulled out of the refrigerator, i.e. the feed amount, is therefore increased. The part of the sample-applying portion of the long test film which was outside the refrigerator is fed to the side downstream of where the sample will be applied, thereby avoiding use of the part of said sample-applying portion which has deteriorated. Accordingly, analyses can be carried out accurately by using parts of the sample-applying portions of the test film which are free of deterioration.

The present invention also provides a second biochemical analysis method comprising the steps of accommodating a long test film containing a reagent layer in a refrigerator, repeatedly pulling said long test film out of said refrigerator until a sample-applying portion, i.e. the next unused portion, of the test film, is aligned with a predetermined sample applying position, sequentially applying liquid samples to the sample-applying portions of said long test film, at which time the sample-applying portions become sample-applied portions and a new sample-applying portion is defined as lying upstream from and adjacent to the sample-applied portion, for each analysis of a sample keeping said sample-applied portions of said long test film at a predetermined temperature for a predetermined time in an incubator, and thereafter irradiating light to said sample-applied portions of said long test film, and finding the optical densities, which depend on how much of a reaction product is formed by a reaction between a liquid sample and a reagent in the reagent layer of the long test film, pulling said sample-applying portions of said long test film back into the refrigerator after an analysis of a sample is finished so that nearly the whole sample-applying portion, positioned on the upstream side of said predetermined sample-applying position, upstream being viewed as the direction opposite the direction in which said long test film is pulled from said refrigerator, is accommodated in said refrigerator, and pulling said sample-applying portions of said long test film out of said refrigerator prior to the next sample application so that said sample-applying portions are aligned with said sample-applying position.

The term "inside a refrigerator" as used herein embraces also a position on a wall of the refrigerator.

With the second biochemical analysis method in accordance with the present invention, when it is expected that the portion of the long test film which is to be used for the next analysis will deteriorate because it will remain outside the refrigerator for too long a period of time before the next sample application and analysis is carried out, almost all of the sample-applying portion is pulled back inside the refrigerator. Therefore, there is no risk of any part of the sample-applying portion's deteriorating even though the period of time prior to the next sample application becomes long. Therefore an accurate analysis can be carried out by use of the test film portions which have not deteriorated.

BRIEF DESCRIPTION OF THE DRAWINGS

FIG. 3 is a schematic view showing the major part of the cross-sectional configuration taken along line X-X' of FIG. 2, FIGS. 4A and 4B are plan views showing the long test film, FIG. 5 is a perspective view showing the film feed cassette and the film wind-up cassette in an apparatus for carrying out the second biochemical analysis method in accordance with the present invention.

DESCRIPTION OF THE PREFERRED EMBODIMENTS

The present invention will hereinbelow be described in further detail with reference to the accompanying drawings.

Figure 1:
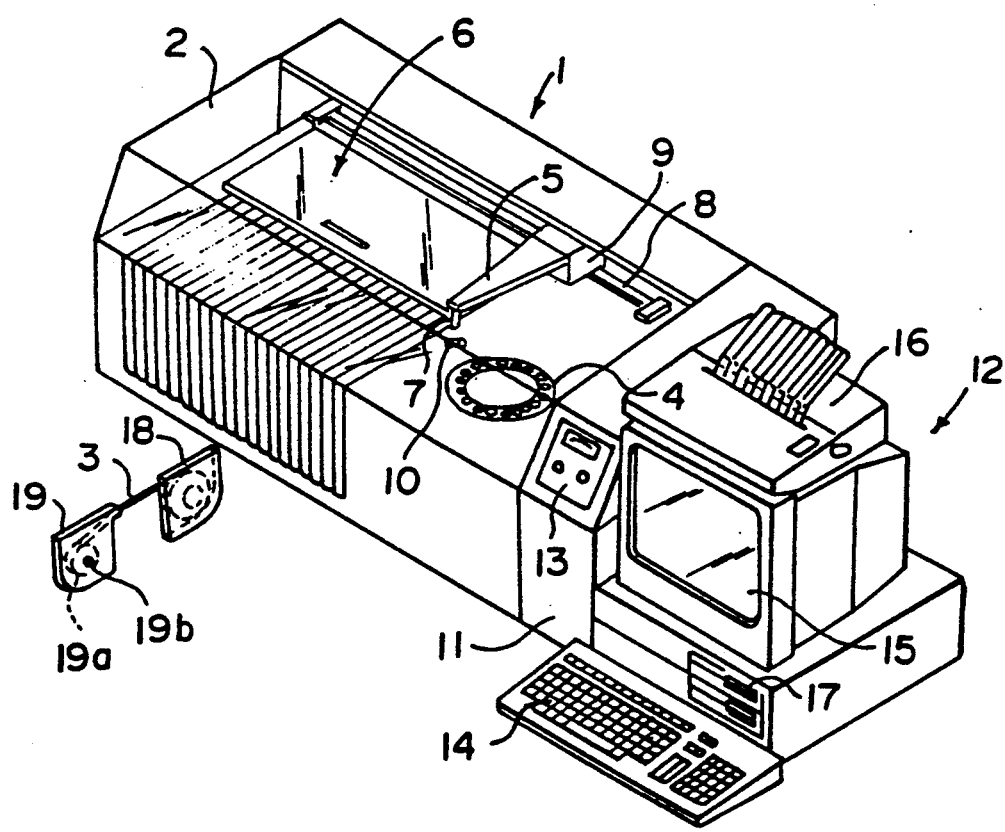
FIG. 1 is a perspective view showing an apparatus for carrying out the first biochemical analysis method in accordance with the present invention.

With reference to FIG. 1, a biochemical analysis apparatus 1 is provided with a transparent cover 2. A liquid sample, a long tape-like test film 3 and the like are fed into and out of the apparatus 1 by opening the cover 2. The apparatus 1 is provided with a sample accommodating means 4 for accommodating a liquid sample such as blood serum or urine around a ring-like structure, and the liquid sample is taken up from the sample accommodating means 4 by a sample application means 5 (as will be described later) and applied onto the long test film 3. The long test film 3 contains a reagent that undergoes a color reaction only with the specific chemical constituent (or the specific physical constituent) of the liquid that is to be analyzed, and many kinds of long test films 3, 3, ... are prepared depending on what the specific chemical constituent to be analyzed is. An unused portion of the long test film 3 which has not yet been used in an analysis of a liquid sample is wound up in a film feed cassette 18, and the used portion of the long test film 3 which has already been used for measurement is wound up in a film wind up cassette 19. At the center of a reel 19a in the film wind-up cassette 19, a hole 19b is provided for engagement with a rotation shaft of a motor for pulling the long test film 3 out of the film feed cassette 18 after the long test film 3 has been accommodated in the biochemical analysis apparatus 1 (as will be described later). The long test film 3 is accommodated in the biochemical analysis apparatus 1 wound up in the film feed cassette 18 and the film wind-up cassette 19. As shown in FIG. 1, the film feed cassette 18 and the film wind-up cassette 19 are formed independently of each other. A test film accommodating means 6 accommodates unused portions of a plurality of the long test films 3, 3, ... in parallel so that various different constituents in liquid samples can be analyzed simultaneously by use of the apparatus 1.

The sample application means 5 is provided with a sample applying nozzle 7 at the end, and is moved along rail 8 by a movement means 9 placed on the rail 8. The nozzle 7 takes up the liquid sample from the sample accommodating means 4, and applies the liquid sample to the long test film 3. The movement means 9 also moves the sample application means 5 vertically. The sample application means 5 is kept at an upper position at the time it is moved by the movement means 9 along rail 8, and is moved down at the time it takes a liquid sample out of the sample accommodating means 4, at the time it applies a sample to the long test film 3 and the time of washing (as will be described later).

After applying the liquid sample to the test film, the sample applying nozzle 7 is washed at a nozzle washing area 10 provided between the test film accommodating means 6 and the sample accommodating means 4. The washed sample applying nozzle 7 is then later reused for sample-application.

The test film to which the liquid sample has already been applied is incubated by an incubator (as will be described later), and subjected to measurement by a measurement means.

Control of operations of the overall apparatus 1, processing of data obtained in the analysis of a liquid sample and the like are carried out by an electronic processing circuit means 11 and a computer 12 connected thereto. An operating and display means 13 on the front surface of the electronic processing circuit means 11 is provided with a power source switch for the apparatus 1, an ammeter for monitoring the current consumption in the apparatus 1, and the like. The computer 12 is provided with a keyboard 14 for giving instructions to the apparatus 1, a CRT display device 15 for displaying subsidiary information related to the instructions given to the apparatus 1, for displaying data from the analysis of a liquid sample and for displaying other items, a printer 16 for printing out data obtained from the analysis of a liquid sample, and a floppy disk drive unit 17 for accommodating a floppy disk for storing commands for giving various instructions to the apparatus 1 and for storing data obtained from the analysis of a liquid sample.

Figure 2:
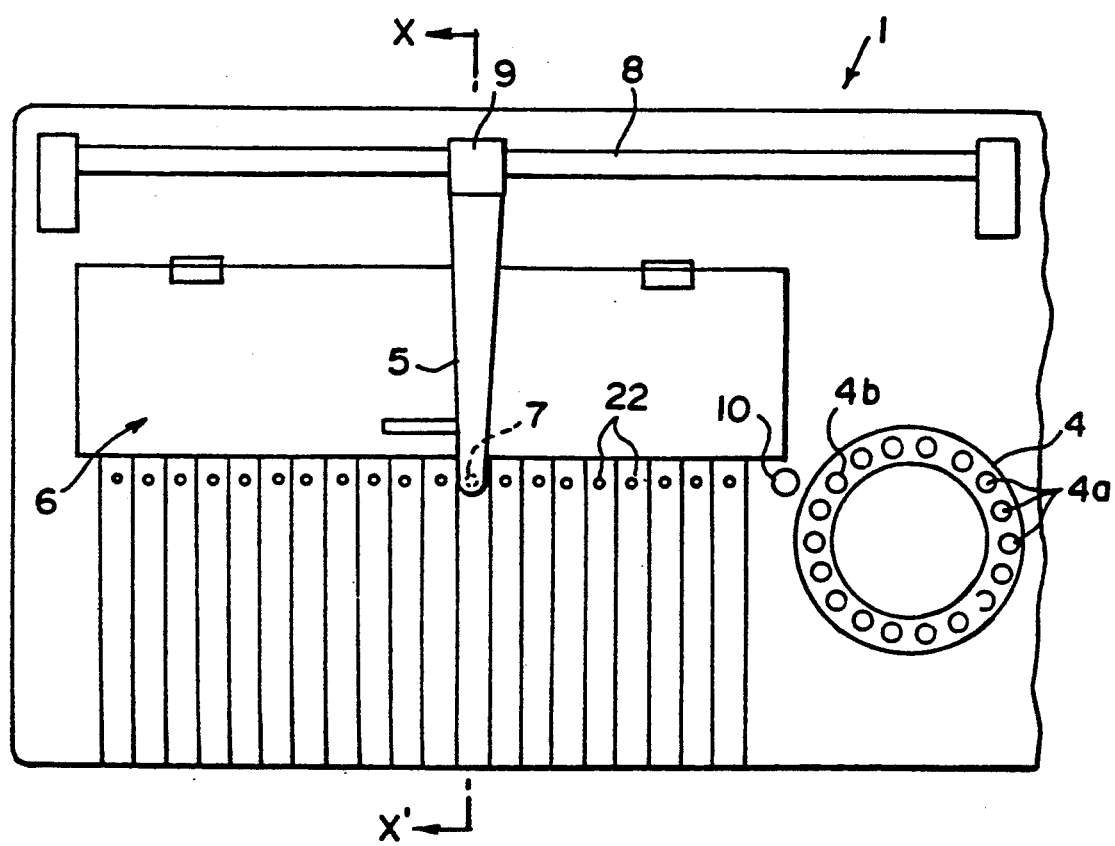
FIG. 2 is a plan view showing the major part of the apparatus shown in FIG. 1.

With reference to FIG. 2, which shows a major part of the apparatus 1, the test film accommodating means 6 is constituted so that an imaginary line formed by connecting the sample applying positions 22, 22, ... for all of the long test films 3, 3, ... is straight. Also, the nozzle washing area 10, and a liquid sample take-out position 4b in the sample accommodating means 4 are disposed on said imaginary line.

The sample accommodating means 4 accommodates a plurality of liquid samples in accommodating regions 4a, 4a, which are in the ring-like structure. The accommodating regions 4a, 4a, ... are automatically rotated by a rotation-means (not shown) until the liquid sample which is accommodated in one of the accommodating regions 4a, 4a, ... and which is to be used in the next analysis arrives at the take-out position 4b. In order to prevent the liquid samples accommodated in the accommodating regions 4a, 4a, ... from evaporating and deteriorating, a cover (not shown) is provided on the accommodating regions 4a, 4a, ... A break in the cover exists at the take-out position 4b.

The sample application means 5 is moved by the movement means 9 along rail 8, takes up the liquid sample from the take-out position 4b, and applies it to a sample applying position 22 on the long test film.

FIG. 3 shows the sectional configuration taken along line X—X' of FIG. 2. In FIG. 3, similar elements are numbered with the same reference numerals with respect to FIG. 1 and 2.

With reference to FIG. 3, the long test film 3 is accommodated in the film feed cassette 18 and the film wind-up cassette 19. The film feed cassette 18 is accommodated in a refrigerator 50 in which the temperature is adjusted to 4° C., by way of example, and the film wind-up cassette 19 is accommodated in a wind-up chamber 51. Because the unused portion of the long test film 3 is accommodated in the film feed cassette 18, the unused long test film 3 can be accommodated in the refrigerator 50 without the hands of an operator contacting the unused long test film 3. The refrigerator 50 is enclosed by a refrigerator wall 50a composed of a heat insulating material. A cooling and dehumidifying device 58 for keeping the inside of the refrigerator 50 at a predetermined low temperature and humidity is provided on one surface of the refrigerator wall 50a, and air inside the refrigerator 50 is circulated by a fan 60.

A rotation shaft of a wind-up motor 53 winds the long test film 3 around the reel 19a of the film wind-up cassette 19 by engaging a hole 19b formed at the center of the reel 19a. As the motor 53 is rotated, the long test film 3 is pulled out of the film feed cassette 18 through a film outlet 50b of the refrigerator 50, and is wound up in the film wind-up cassette 19.

Because the used long test film 3 is accommodated in the film wind-up cassette 19, it can be taken out of the apparatus 1 and discarded or processed for other purposes without the hands of the operator contacting it.

Instead of winding up the used film in the film wind-up cassette 19, the film wind-up cassette 19 may be omitted, and a box for receiving the film may be provided in the wind-up chamber 51. The box is capable of being inserted into and removed from apparatus 1. A cutter for cutting the used film may be provided near the inlet of the region of the wind-up chamber 51, and the used film may be cut and stored in the box. With this configuration, the used film stored in the box can be taken out of the apparatus 1 by removing the box, so that the used film may be discarded or processed for other purposes without the hands of an operator contacting it. In this case, the test film may be pulled from the film-feed cassette 18 by conveying rollers for grasping and conveying the test film.

An incubator 55 in which the long test film 3 incubates and through which the long test film 3 then passes is provided between the film-feed cassette 18 and the film wind-up cassette 19. A measuring device 57 is provided for finding the optical density produced when the long test film 3 is irradiated after the liquid sample is applied and the portion of the long test film to which the sample has been applied is incubated in the incubator 55.

The long test film 3 is intermittently pulled out of the refrigerator 50 by the operation of the motor 53, and intermittently fed leftward in FIG. 3. Prior to this step, an upper cover 55a of the incubator 55 is moved up in the direction indicated by arrow A. After the long test film 3 is moved forward (to the left in FIG. 3), the upper cover 55a is moved down in the direction indicated by arrow B. The downward action of the upper cover 55a pushes down the long test film 3. Then, a shutter 54, covering a hole 55b in the upper cover 55a through which the sample applying nozzle 7 is to be inserted is moved rightward, and the sample applying nozzle 7 is moved down as illustrated to apply a liquid sample onto the long test film 3 through the hole 55b. Thereafter, the shutter 54 is moved leftward to cover the hole 55b and prevent air flow between the inside and outside of the incubator 55, and the temperature in the incubator 55 is maintained at a predetermined level, for example, 37° C. The film portion to which the liquid sample has been applied and spread, as indicated by hatching in FIG. 3, is incubated for a predetermined time (four minutes, for example) in the incubator 55. In the course of the incubation or after the incubation is finished, the optical density at the portion of the long test film 3 to which the liquid sample has already been applied is found by the measuring device 57. The density is found by irradiating light produced by a light irradiation means 57a, which light has a wavelength selected in advance, onto the long test film 3, and detecting the light reflected by the long test film 3 by use of a photodetector 57b.

Application of the next liquid sample becomes possible after the application, incubation and analysis of a single liquid sample are completed in the manner described above. The long test film 3 remains inside the incubator 55 after the aforesaid analysis is finished, and is moved just prior to a sample application for the next analysis so that a film portion which is to be used for the next analysis is brought to the sample applying position.

FIG. 4A shows the relationship between the position of the long test film 3 and the position of the incubator 55, the sample applying position (the position of the nozzle 7), and the position of the refrigerator 50. A portion 3a of the long test film 3 is one to which a liquid sample has already been applied, and at which the analysis of the sample is finished. A portion 3b is to be fed to the sample applying position as the long test film 3 is moved. To portion 3b the next liquid sample is to be applied. In this case, the length of the portion of the long test film 3 necessary for a single analysis step is equal to l. As is clear from FIG. 4A, the film outlet of the refrigerator 50 and the sample applying position are spaced apart from each other to some extent, and part of the film portion 3b which is to be used in the next sample analysis is located outside the refrigerator 50. Particularly, with the aforesaid apparatus, wherein a gap 59 is present between the refrigerator 50 and the incubator 55, it is difficult to keep the film portion positioned in the gap 59 at a desirable temperature and humidity. When many liquid samples are to be analyzed and the analyses of the liquid samples are carried out sequentially, the time during which the film portion 3b remains outside the refrigerator 50 may be as short as four minutes (i.e. the time required for incubation), and therefore no problem arises. However, when the time between analyses of consecutively applied samples becomes long, the long test film 3 deteriorates where it is exposed at the gap 59, and an accurate analysis of a sample therefore cannot be carried out. When the time between two consecutive sample analyses becomes even longer, deterioration of the long test film 3 progresses to the film portion located beyond the refrigerator wall 50a shown in FIG. 3. Accordingly, in the first biochemical analysis method in accordance with the present invention, the length of a film feed amount which is fed just prior to the application of a next sample to be analyzed is set depending on conditions, such as the time which has elapsed from the application of a last prior sample, thereby to avoid using a deteriorated film portion in an analysis. The extent to which the length of the film feed amount is increased or decreased may be adjusted in accordance with various setting conditions. For example, in the case where the length of the portion of the long test film 3 necessary for a single analysis step is equal to l and the time between sample applications becomes longer than a predetermined time, the length of the feed amount of the long test film 3, which is fed prior to the next sample application, is adjusted to be 2l, i.e. the ordinary length l plus a further length l, as shown in FIG. 4B. In this case, as the feed amount is equal to 2l, a portion denoted by 3b' is used as the portion on which the liquid sample is to be applied for analysis. Therefore, the deteriorated film portion is fed to the downstream side of the sample applying position and is not used in an analysis, and the accuracy of the next sample analysis is not affected adversely. The criterion for judging whether the time between sample application is too long, which determines whether the length of the feed amount is to be or is not to be increased, may be selected arbitrarily. For example, in the case where analyses are carried out frequently during a day, the length of the film feed amount may be increased to 2l at the time the daily operation of the apparatus is begun.

Also, several kinds of test films are used in accordance with the constituents to be analyzed in the liquid samples, and the degree of deterioration caused by too high a temperature and humidity differs in accordance with the kind of test film used. Table 1 shows examples of the relative degree of deterioration for different constituents (which affect the choice of the type of test film) of a liquid sample, the quantities of which constituents are to be analyzed.

TABLE 1

| Degree of deterioration | Constituent of liquid sample to be analyzed |
| --- | --- |
| Low | Uric acid (UA), albumin (ALB) |
| Comparatively low | γ-Glutamyl transpeptidase (GGT), alanine aminotransferase (GPT), alkali phosphatase (ALP) |
| Comparatively high | Total cholesterol (TCHO) neutral fat (TG), urea nitrogen (BUN) |
| High | Creatinine (CRE), total bilirubin (TBIL) |

Accordingly, when and by how much the length of the feed amount is changed depends on the kind of test film used. For example, the length of the feed amount may be adjusted to 2l when using test films for analyzing UA, ALB, GGT, GPT and ALP, which exhibit a low degree of deterioration or a comparatively low degree of deterioration, and may be adjusted to 3l when using test films for analyzing TCHO, TG, BUN, CRE and TBIL, which exhibit a high degree of deterioration or a comparatively high degree of deterioration. Also, the extent of the increase in the length of the feed amount need not necessarily be integer multiples of a predetermined feed amount, but the length of the feed amount must be set so that at least the deteriorated film portion is fed to the downstream side of the sample applying position. In any case, the length of the feed amount may be increased as required by providing an operating means to control the motor 53.

Furthermore, when the frequency of use of the apparatus is not constant and the apparatus often remains unused for many days, the extent to which the length of the feed amount is increased in the first a of a series of analyses of samples may be changed in accordance with the kind of test film used and the time (the number of days) elapsed since the last prior analysis of a sample was conducted. Table 2 shows examples of the feed amounts in accordance with the elapsed time and the kind of test film used (the multiple of a predetermined feed amount 1 for a single sample analysis, which is inherent to the kind of test film, and an additional feed amount). In Table 2, the kind of test film is represented by the constituent in a liquid sample, whose quantity is to be found, and the values denote the length of the feed amount relative to a predetermined feed amount l inherent to each type of test film which is normalized to 1.

time between consecutive sample applications may be taken into account when setting the length of the feed amount. By way of example, the length of the feed amount, l, may be expressed by:

$$L = \left\{ \text{INT}\left[ \frac{1}{K} \times \frac{\sum_{i=1}^{n} Ti \times Hi}{24 \times 25 \times 50} \right] + 1 \right\} l$$

where Ti denotes the environmental temperature measured at intervals of one hour up to n hours which have elapsed after the last prior analysis of a liquid sample was finished (for example, Ti could represent the temperature at the gap 59, in units of ° C.), Hi denotes the environmental humidity (in units of %) measured at the same times as the environmental temperature Ti, K denotes a constant determined in accordance with the kind of test film used, INT[ ] denotes an integer obtained by counting fractions below zero in []as a whole number, 24 represents 24 hours, 25 is the standard temperature, and 50 is the standard humidity (%). The constant K is equal to 2 for the CRE and TBIL test films, 4 for the TCHO, TG and BUN test films, 10 for the GGT, GPT and GOT test films and 30 for the UA and ALB test films.

When the length of the film feed amount is adjusted in accordance with the elapsed time measured from the last prior sample application, the temperature and the humidity, a timer, a temperature sensor and a humidity sensor should preferably be provided, and the motor for pulling the long test film out of the film feed cassette should preferably be controlled automatically, based on the outputs of these means prior to a next sample application. Also, the relationship between the length of the feed amount and the elapsed time, the temperature and humidity may be determined in various ways other than by using the formula shown above.

An apparatus for carrying out the second biochemical analysis method in accordance with the present invention will be described hereinbelow.

In this case, the film feed cassette 18 and the film wind-up cassette 19 as shown in FIG. 5 are used in the biochemical analysis apparatus 1 shown in FIG. 1. As mentioned above, a hole 19b is provided at the center of the reel 19a in the film wind-up cassette 19 for engagement with the rotation shaft of a motor for pulling the long test film 3 out of the film feed cassette 18 after the long test film 3 has been accommodated in the biochemical analysis apparatus 1. Also, in this embodiment of the present invention a hole 18b is provided at the center of a reel 18a in the film feed cassette 18 for engagement with a rotation shaft of a motor for winding the long test film 3 back into the film feed cassette 18.

Figure 6:
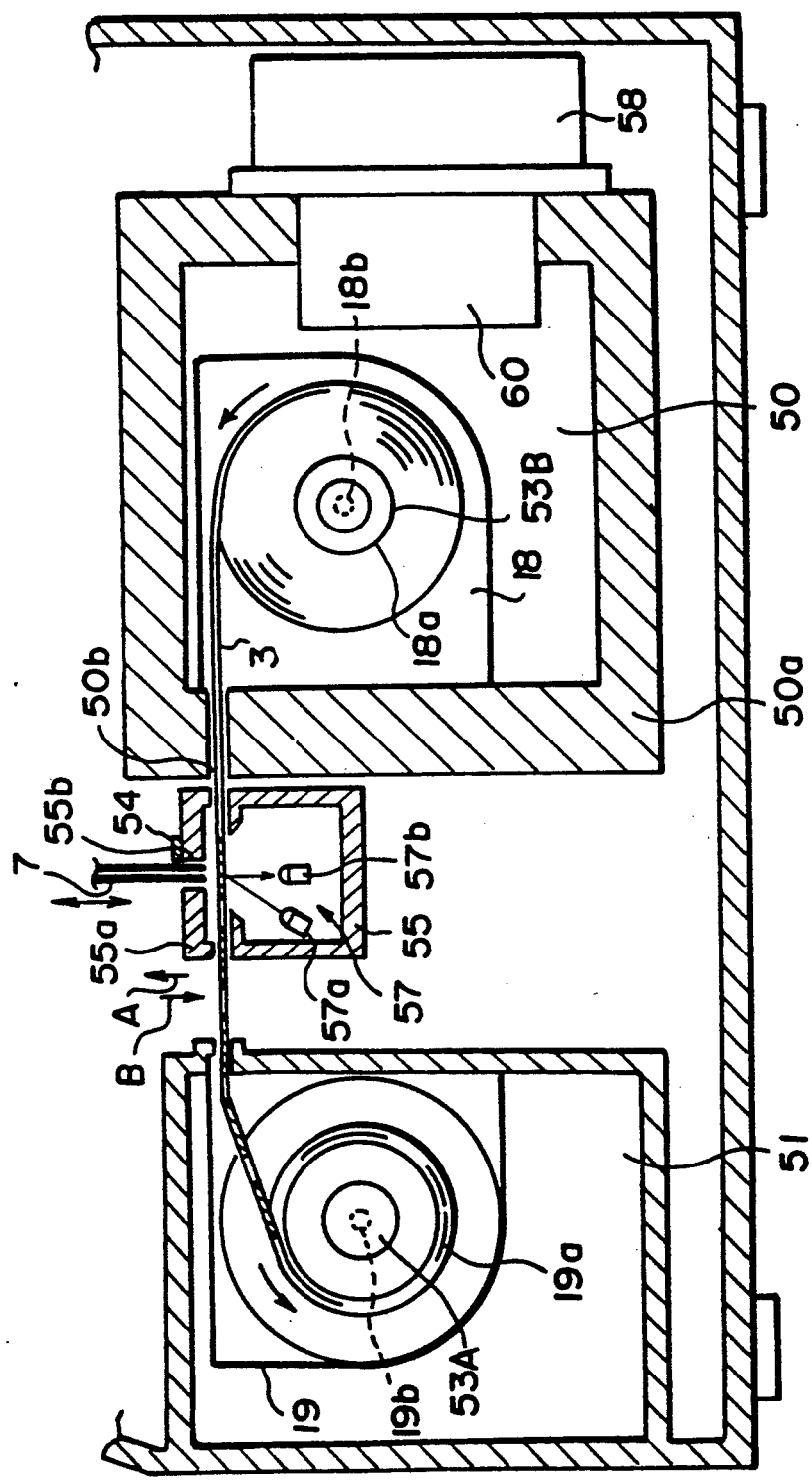
FIG. 6 is a schematic view showing the major part of the cross-sectional configuration of the apparatus for carrying out the second biochemical analysis method in accordance with the present invention.

FIG. 6 shows a major part of the cross-sectional configuration of the apparatus for carrying out the second biochemical analysis method in accordance with the present invention taken along line X—X' of FIG. 2.

TABLE 2

| Kind of test film | Elapsed time t (days) | | | | | |
| --- | --- | --- | --- | --- | --- | --- |
| | t < 1 | 1 < t < 2 | 2 < t < 4 | 4 < t < 10 | 10 < t < 20 | 20 < t < 30 |
| CRE.TBIL | 1 | 2 | 3 | 4 | 5 | 6 |
| TCHO.TG.BUN | 1 | 1 | 2 | 3 | 4 | 4 |
| GGT.GPT.GOT | 1 | 1 | 1 | 2 | 3 | 3 |
| UA.ALB | 1 | 1 | 1 | 1 | 1 | 2 |

In the case where the length of the feed amount of the long test film is to be adjusted even more accurately, the temperature and the humidity as well as the elapsed In FIG. 6, similar elements are numbered with the same reference numerals with respect to FIG. 3.

When the film feed cassette 18 and the film wind-up cassette 19 are accommodated in the refrigerator 50 and the wind-up chamber 51, respectively, a rotation shaft of a wind up motor 53A, which motor is provided in the wind-up chamber 51, is engaged with the hole 19b formed at the center of the reel 19a of the film wind-up cassette 19. As the motor 53A rotates, the long test film 3 is pulled out of the film feed cassette 18 through the film outlet 50b of the refrigerator 50, and is wound up in the film wind-up cassette 19. On the other hand, a rotation shaft of a motor 53B for winding the long test film 3 back into the film feed cassette 18 (as will be described later) is engaged with the hole 18b at the center of the reel 18a of the film feed cassette 18.

In the same manner as in the embodiment shown in FIG. 3, the long test film 3 is intermittently pulled out of the refrigerator 50 by the operation of the motor 53A, and sample application, incubation and analysis are carried out.

Figure 7A:
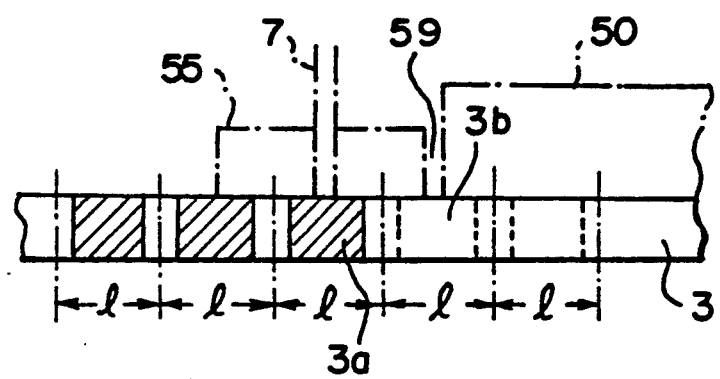
FIGS. 7A, 7B and 7C are plan views showing the long test film.
Figure 7B:
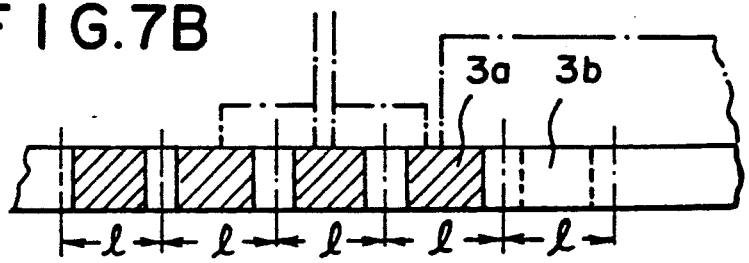
Figure 7C:
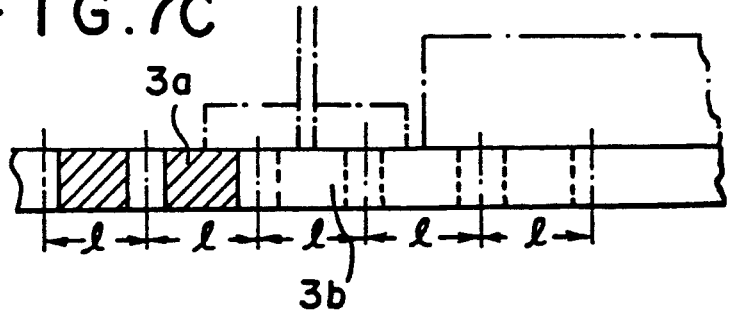

FIG. 7A shows the relationship between the position of the long test film 3 and the position of the incubator 55, the sample applying position (the position of nozzle 7), and the position of the refrigerator 50. The liquid sample has already been applied to portion 3a of the long test film 3, and the analysis of the liquid sample has been finished. Portion 3b is to be fed to the sample applying position as the long test film 3 is moved. To portion 3b the next liquid sample is to be applied. In this case, the length of the portion of the long test film 3 necessary for an analysis of a single liquid sample is equal to 1. As mentioned above with reference to FIG. 4A, when the time between the applications of two consecutive samples becomes long, the long test film 3 deteriorates where it is exposed at the gap 59, and an accurate analysis of a sample cannot be carried out at deteriorated portions of the test film. Accordingly, in the second biochemical analysis method in accordance with the present invention, when a predetermined time has elapsed after an analysis of one sample and before application of a second next sample to the test film, the motor 53B engaged with the film feed cassette 18 is operated to rotate the reel 18a clockwise so that the film portion 3b which is to be used in the analysis of a next sample is returned to the inside of the refrigerator 50. The predetermined time at which the test film is wound back and the amount of the test film which is wound back may be arbitrarily chosen in accordance with the configuration of the apparatus and the working environment. In this embodiment, a length of the long test film 3 equaling 1, as shown in FIG. 7B, is wound back when, for example, two hours have elapsed since the analysis of the last prior sample was conducted. An instruction causing the test film to be wound back may be issued manually by an operator of the apparatus 1, or automatically through the provision of a timer in the apparatus. Since a length 1 of the long test film 3 is returned to the refrigerator in this manner, the film portion 3b which is to be used in the next sample analysis is not left standing outside the refrigerator 50 for more than two hours, and therefore does not deteriorate to such an extent that a problem arises. When the next sample is to be analyzed, the motor 53A is controlled to pull out the long test film 3 by a distance equal to the length 2l, i.e. the sum of the length by which the long test film 3 was wound back and the length which is to be used in the analysis of the next sample, as shown in FIG. 7C. The film portion 3b thus brought to the sample applying position was kept in the refrigerator 50 until just prior to its use in the analysis of a sample, and therefore an accurate analysis can be carried out by use of the film portion 3b, which is free of deterioration. The predetermined time (two hours) may be changed in accordance with the kind of long test film 3 used. If the time between the application of two consecutive samples to the long test film 3 becomes even longer, although a length 1 of the long test film has been wound back into the refrigerator 50, deterioration of the long test film 3 may progress to the film portion beyond the refrigerator wall 50a shown in FIG. 6. In this case, the long test film 3 may be pulled out by a length slightly longer than 2l prior to the next sample application so that the deteriorated film portion is fed to the downstream side of the sample applying position as viewed in the direction in which the test film is pulled out. Also, the length of the test film which is wound back need not necessarily be equal to 1. For example, if the film portion 3a on which the liquid sample has already been applied should not enter the film outlet of the refrigerator 50, the length of the test film, which is wound back, may be adjusted to approximately 1/2. Furthermore, it would be necessary for the length of the test film, which is wound back, to be increased if the distance between the film outlet of the refrigerator 50 and the sample applying position were longer.

In the case where analyses are carried out frequently during a day, instead of adjusting the length of the long test film 3 to be wound back on the basis of the passage of a predetermined time, the long test film 3 may be wound back by a predetermined length at the time the daily operation of the apparatus is finished. When the length of time between consecutive sample applications cannot be anticipated, the long test film 3 may be wound back each time the analysis of a sample is finished.

We claim:

1. A biochemical analysis method comprising the steps of:

positioning an elongated test film containing a reagent layer in a refrigerator, repeatedly pulling said elongated test film out of said refrigerator by a predetermined length until a sample-applying portion of said elongated test film is aligned with a predetermined sample applying position, sequentially applying liquid samples to respective ones of sample-applying portions of said elongated test film at said sample applying position so that said sample-applying portions become sample-applied portions and a new sample-applying portion is defined as lying upstream from and adjacent to the sample-applied portion to which a last prior sample was applied, for each analysis of a liquid sample, incubating each of said sample-applied portions of said elongated test film at a predetermined temperature for a predetermined time in an incubator, irradiating light to each of said sample-applied portions of said elongated test film having been incubated, and measuring an optical density of each of said sample-applied portions having been incubated based on a reaction product formed by a reaction between a respective liquid sample applied to said sample-applied portions of said elongated test film and a reagent in the reagent layer of said elongated test film, and increasing a length of the sample-applying portion which is pulled out of said refrigerator prior to a next sample application to said elongated test film depending upon environmental conditions outside of said refrigerator occurring after a last measurement of said optical density has been finished and an amount of time said new sample-applying portion is exposed to said environmental conditions, said length being greater than said predetermined length.

2. A method as defined in claim 1 wherein said length of the sample-applying portion of said long test film is determined in accordance with a time elapsed since an analysis of a last prior a sample and with the kind of long test film used.

3. A method as defined in claim 1 wherein said length of the sample-applying portion of said long test film which is pulled out of said refrigerator is determined in accordance with a time elapsed since an analysis of a last prior sample and with the humidity, the temperature, and the kind of long test film used.

4. A biochemical analysis method comprising the steps of:

positioning an elongated test film containing a reagent layer in a refrigerator, repeatedly pulling said elongated test film out of said refrigerator by a predetermined length until a respective sample-applying portion of said elongated test film is aligned with a predetermined sample applying position, sequentially applying liquid samples to respective ones of said sample-applying portion of said elongated test film at said predetermined sample applying position so that said sample-applying portions become sample-applied portions and a new sample-applying portion is defined as lying upstream from and adjacent to the sample-applied portion to which a last prior sample was applied, for each analysis of a sample, incubating said sample-applied portions of said elongated test film at a predetermined temperature for a predetermined time in an incubator, irradiating light to said sample-applied portions of said elongated test film having been incubated, and measuring an optical density of each of said sample-applying portions having been incubated, said optical density being based on a reaction product formed by a reaction between a liquid sample applied to said sample-applied portions of said elongated test film and a reagent in the reagent layer of said elongated test film.

pulling said sample-applying portions of said elongated test film back into the refrigerator by at least said predetermined length depending upon environmental conditions outside of said refrigerator occurring after an analysis of a sample is finished and an amount of time said new sample-applying portion is exposed to said environmental conditions so that substantially the entire sample-applying portion that has been positioned on the upstream side of said predetermined sample applying position, upstream being viewed as the direction opposite to the direction in which said elongated test film is pulled out from said refrigerator, is pulled back into said refrigerator to prevent deterioration of said sample-applying portion which has been positioned on the upstream side of said predetermined sample applying position, and pulling said sample-applying portions of said elongated test film out of said refrigerator by a length greater than said predetermined length depending upon environmental conditions outside of said refrigerator occurring after a last measurement of said optical density has been finished and an amount of time said new sample-applying portion is exposed to said environmental conditions prior to a next sample application so that respective ones of said sample-applying portions are aligned with said predetermined sample applying position.

5. A method according to claim 4, further comprising a step of determining an amount of said sample-applying portion to be pulled out of said refrigerator in accordance with an elapsed, predetermined amount of time.

6. A method according to claim 4, further comprising a step of determining an amount of said sample-applying portion to be pulled out in accordance with an elapsed, predetermined amount of time and a type of said long test film used.

7. A method according to claim 4, further comprising a step of determining an amount of said sample-applying portion to be pulled out in accordance with an elapsed, predetermined amount of time, a type of said long test film used, and a type of constituent on said sample-applying portion of said long test film.

8. A method according to claim 4, wherein said step of pulling back said sample-applying portions of said long test film is performed automatically after a predetermined time has elapsed.

9. A method according to claim 4, wherein said step of pulling back said sample-applying portions of said long test film is performed manually.

* * * * *